US009364212B2

(12) United States Patent
Catanese, III et al.

(10) Patent No.: US 9,364,212 B2
(45) Date of Patent: Jun. 14, 2016

(54) SUTURE ANCHORING DEVICES AND METHODS FOR USE

(71) Applicant: Neotract, Inc., Pleasanton, CA (US)

(72) Inventors: Joseph Catanese, III, San Leandro, CA (US); Floria Cheng, San Francisco, CA (US); Daniel Merrick, Dublin, CA (US); Ling-Kang Tong, Fremont, CA (US); Michael Gearhart, Fremont, CA (US); Matthew McLean, San Francisco, CA (US); James Niederjohn, San Jose, CA (US); Brian Y. Tachibana, Oakland, CA (US); Ben Thompson, San Carlos, CA (US)

(73) Assignee: NeoTract, Inc., Pleasanton, CA (US)

( * ) Notice: Subject to any disclaimer, the term of this patent is extended or adjusted under 35 U.S.C. 154(b) by 371 days.

(21) Appl. No.: 13/830,232

(22) Filed: Mar. 14, 2013

(65) Prior Publication Data

US 2013/0268001 A1 Oct. 10, 2013

Related U.S. Application Data

(63) Continuation-in-part of application No. 12/791,805, filed on Jun. 1, 2010, now Pat. No. 8,603,106, which is a continuation-in-part of application No. 11/492,690, filed on Jul. 24, 2006, now Pat. No. 7,896,891, which (Continued)

(51) Int. Cl.
*A61B 17/10* (2006.01)
*A61B 17/04* (2006.01)
*A61B 17/02* (2006.01)

(Continued)

(52) U.S. Cl.
CPC ......... *A61B 17/0401* (2013.01); *A61B 17/0218* (2013.01); *A61B 17/0487* (2013.01); *A61B 17/0643* (2013.01); *A61B 2017/00274* (2013.01); *A61B 2017/00477* (2013.01); *A61B 2017/00805* (2013.01); *A61B 2017/00862* (2013.01); *A61B 2017/0404* (2013.01);

(Continued)

(58) Field of Classification Search
CPC .................. A61B 17/0401; A61B 2017/0404; A61B 2017/0417
See application file for complete search history.

(56) References Cited

U.S. PATENT DOCUMENTS 659,422 A 10/1900 Shidler
780,392 A 1/1905 Wanamaker (Continued)

FOREIGN PATENT DOCUMENTS

DE 10159470 A1 6/2003
EP 0246836 12/1991

(Continued)

OTHER PUBLICATIONS

Bachavora, O.A., "The Effect of Rhodiolae Rosea Extract on Incidence Rate of Superficial Bladder Carcinoma Relapses", Kozin, (1995), 3 pgs.

(Continued)

*Primary Examiner* — Gregory Anderson

(57) ABSTRACT

A system and associated method for manipulating tissues and anatomical or other structures in medical applications for the purpose of treating diseases or disorders or other purposes. An implant for attachment of soft tissue to bone, an insertion tool for anchoring suture anchors to bone, and a method for anchoring a suture anchor to bone.

4 Claims, 8 Drawing Sheets

Related U.S. Application Data is a continuation-in-part of application No. 11/318,246, filed on Dec. 22, 2005, now Pat. No. 7,645,286, which is a continuation-in-part of application No. 11/134,870, filed on May 20, 2005, now Pat. No. 7,758,594.

(60) Provisional application No. 61/707,752, filed on Sep. 28, 2012.

(51) Int. Cl.
*A61B 17/00* (2006.01)
*A61B 18/00* (2006.01)
*A61B 17/064* (2006.01)

(52) U.S. Cl.
CPC *A61B 2017/0417* (2013.01); *A61B 2017/0464* (2013.01); *A61B 2018/00547* (2013.01)

(56) References Cited

U.S. PATENT DOCUMENTS

| | | | |
|---|---|---|---|
| 789,467 A | 5/1905 | West | |
| 2,579,192 A | 12/1951 | Kohl | |
| 2,646,298 A | 7/1953 | Leary | |
| 2,697,624 A | 12/1954 | Thomas | |
| 2,734,299 A | 2/1956 | Masson | |
| 2,825,592 A | 3/1958 | McKenzie | |
| 3,326,586 A | 6/1967 | Frost | |
| 3,470,834 A | 10/1969 | Bone | |
| 3,521,918 A | 7/1970 | Hammond | |
| 3,713,680 A | 1/1973 | Pagano | |
| 3,716,058 A | 2/1973 | Tanner | |
| 3,756,638 A | 9/1973 | Stockberger | |
| 3,873,140 A | 3/1975 | Bloch | |
| 3,875,648 A | 4/1975 | Bone | |
| 3,931,667 A | 1/1976 | Merser | |
| 3,976,079 A | 8/1976 | Samuels | |
| 4,006,747 A | 2/1977 | Kronenthal | |
| 4,210,148 A | 7/1980 | Stivala | |
| 4,235,238 A | 11/1980 | Ogiu | |
| 4,291,698 A | 9/1981 | Fuchs | |
| 4,409,974 A | 10/1983 | Freedland | |
| 4,493,323 A | 1/1985 | Albright | |
| 4,513,746 A | 4/1985 | Aranyi | |
| 4,621,640 A | 11/1986 | Mulhollan | |
| 4,657,461 A | 4/1987 | Smith | |
| 4,669,473 A | 6/1987 | Richards | |
| 4,705,040 A | 11/1987 | Mueller | |
| 4,714,281 A | 12/1987 | Peck | |
| 4,738,255 A | 4/1988 | Goble | |
| 4,741,330 A | 5/1988 | Hayhurst | |
| 4,744,364 A | 5/1988 | Kensey | |
| 4,750,492 A | 6/1988 | Jacobs | |
| 4,762,128 A | 8/1988 | Rosenbluth | |
| 4,823,794 A | 4/1989 | Pierce | |
| 4,899,743 A | 2/1990 | Nicholson | |
| 4,926,860 A | 5/1990 | Stice | |
| 4,946,468 A | 8/1990 | Li | |
| 4,955,913 A | 9/1990 | Robinson | |
| 4,968,315 A | 11/1990 | Gatturna | |
| 5,002,550 A | 3/1991 | Li | |
| 5,041,129 A | 8/1991 | Hayhurst | |
| 5,046,513 A | 9/1991 | Gatturna | |
| 5,053,046 A | 10/1991 | Janese | |
| 5,100,421 A | 3/1992 | Christoudias | |
| 5,123,914 A | 6/1992 | Cope | |
| 5,129,912 A | 7/1992 | Noda | |
| 5,192,303 A | 3/1993 | Gatturna | |
| 5,203,787 A | 4/1993 | Noblitt | |
| 5,207,672 A | 5/1993 | Roth | |
| 5,217,470 A | 6/1993 | Weston | |
| 5,217,486 A | 6/1993 | Rice | |
| 5,234,454 A | 8/1993 | Bangs | |
| 5,236,445 A | 8/1993 | Hayhurst | |
| 5,258,015 A | 11/1993 | Li | |
| 5,269,809 A | 12/1993 | Hayhurst | |
| 5,330,488 A | 7/1994 | Goldrath | |
| 5,334,200 A | 8/1994 | Johnson | |
| 5,336,240 A | 8/1994 | Metzler | |
| 5,354,271 A | 10/1994 | Voda | |
| 5,358,511 A | 10/1994 | Gatturna | |
| 5,364,408 A | 11/1994 | Gordon | |
| 5,366,490 A | 11/1994 | Edwards | |
| 5,368,599 A | 11/1994 | Hirsch | |
| 5,370,646 A | 12/1994 | Reese | |
| 5,380,334 A | 1/1995 | Torrie | |
| 5,391,182 A | 2/1995 | Chin | |
| 5,403,348 A | 4/1995 | Bonutti | |
| 5,405,352 A | 4/1995 | Weston | |
| 5,411,520 A | 5/1995 | Nash | |
| 5,417,691 A | 5/1995 | Hayhurst | |
| 5,435,805 A | 7/1995 | Edwards | |
| 5,470,337 A | 11/1995 | Moss | |
| 5,472,446 A | 12/1995 | de la Torre | |
| 5,480,406 A | 1/1996 | Nolan | |
| 5,499,994 A | 3/1996 | Tihon | |
| 5,501,690 A | 3/1996 | Measamer | |
| 5,507,754 A | 4/1996 | Green | |
| 5,522,846 A | 6/1996 | Bonutti | |
| 5,531,763 A | 7/1996 | Mastri | |
| 5,534,012 A * | 7/1996 | Bonutti | 606/232 |
| 5,536,240 A | 7/1996 | Edwards | |
| 5,540,704 A | 7/1996 | Gordon | |
| 5,545,171 A | 8/1996 | Sharkey | |
| 5,545,178 A | 8/1996 | Kensey | |
| 5,550,172 A | 8/1996 | Regula | |
| 5,554,162 A | 9/1996 | DeLange | |
| 5,554,171 A | 9/1996 | Gatturna | |
| 5,562,689 A | 10/1996 | Green | |
| 5,569,305 A | 10/1996 | Bonutti | |
| 5,571,104 A | 11/1996 | Li | |
| 5,573,540 A | 11/1996 | Yoon | |
| 5,578,044 A | 11/1996 | Gordon | |
| 5,591,177 A | 1/1997 | Lehrer | |
| 5,593,421 A | 1/1997 | Bauer | |
| 5,611,515 A | 3/1997 | Benderev | |
| 5,626,614 A | 5/1997 | Hart | |
| 5,630,824 A | 5/1997 | Hart | |
| 5,643,321 A * | 7/1997 | McDevitt | 606/232 |
| 5,647,836 A | 7/1997 | Blake | |
| 5,665,109 A | 9/1997 | Yoon | |
| 5,667,486 A | 9/1997 | Mikulich | |
| 5,669,917 A | 9/1997 | Sauer | |
| 5,690,649 A | 11/1997 | Li | |
| 5,690,677 A | 11/1997 | Schmieding | |
| 5,697,950 A | 12/1997 | Fucci | |
| 5,707,394 A | 1/1998 | Miller | |
| 5,716,368 A | 2/1998 | de la Torre | |
| 5,718,717 A | 2/1998 | Bonutti | |
| 5,725,556 A | 3/1998 | Moser | |
| 5,725,557 A | 3/1998 | Gatturna | |
| 5,733,306 A | 3/1998 | Bonutti | |
| 5,741,276 A | 4/1998 | Poloyko | |
| 5,746,753 A | 5/1998 | Sullivan | |
| 5,749,846 A | 5/1998 | Edwards | |
| 5,752,963 A | 5/1998 | Allard | |
| 5,782,862 A | 7/1998 | Bonutti | |
| 5,782,864 A | 7/1998 | Lizardi | |
| 5,800,445 A | 9/1998 | Ratcliff | |
| 5,807,403 A | 9/1998 | Beyar | |
| 5,810,848 A | 9/1998 | Hayhurst | |
| 5,814,072 A | 9/1998 | Bonutti | |
| 5,830,179 A | 11/1998 | Mikus | |
| 5,830,221 A | 11/1998 | Stein | |
| 5,845,645 A | 12/1998 | Bonutti | |
| 5,846,254 A | 12/1998 | Schulze | |
| 5,861,002 A | 1/1999 | Desai | |
| 5,868,762 A | 2/1999 | Cragg | |
| 5,873,891 A | 2/1999 | Sohn | |
| 5,897,574 A | 4/1999 | Bonutti | |
| 5,899,911 A | 5/1999 | Carter | |
| 5,899,921 A | 5/1999 | Caspari | |
| 5,904,696 A | 5/1999 | Rosenman | |

(56) References Cited

U.S. PATENT DOCUMENTS

| | | |
|---|---|---|
| 5,908,428 A | 6/1999 | Scirica |
| 5,919,198 A | 7/1999 | Graves |
| 5,919,202 A | 7/1999 | Yoon |
| 5,921,986 A | 7/1999 | Bonutti |
| 5,928,252 A | 7/1999 | Steadman |
| 5,931,844 A | 8/1999 | Thompson |
| 5,944,739 A | 8/1999 | Zlock |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Willard |
| 5,971,447 A | 10/1999 | Steck |
| 6,010,514 A | 1/2000 | Burney |
| 6,011,525 A | 1/2000 | Piole |
| 6,030,393 A | 2/2000 | Corlew |
| 6,033,430 A | 3/2000 | Bonutti |
| 6,036,701 A | 3/2000 | Rosenman |
| 6,048,351 A | 4/2000 | Gordon |
| 6,053,908 A | 4/2000 | Crainich |
| 6,056,722 A | 5/2000 | Jayaraman |
| 6,056,772 A | 5/2000 | Bonutti |
| 6,066,160 A | 5/2000 | Colvin |
| 6,068,648 A | 5/2000 | Cole |
| 6,080,167 A | 6/2000 | Lyell |
| 6,086,608 A | 7/2000 | Ek |
| 6,110,183 A | 8/2000 | Cope |
| 6,117,160 A | 9/2000 | Bonutti |
| 6,117,161 A | 9/2000 | Li |
| 6,120,539 A | 9/2000 | Eldridge |
| 6,139,555 A | 10/2000 | Hart |
| RE36,974 E | 11/2000 | Bonutti |
| 6,143,006 A | 11/2000 | Chan |
| 6,152,935 A | 11/2000 | Kammerer |
| 6,159,234 A | 12/2000 | Bonutti |
| 6,200,329 B1 | 3/2001 | Fung |
| 6,206,895 B1 | 3/2001 | Levinson |
| 6,228,096 B1 | 5/2001 | Marchand |
| 6,258,124 B1 | 7/2001 | Darois |
| 6,261,302 B1 | 7/2001 | Voegele |
| 6,270,530 B1 | 8/2001 | Eldridge |
| 6,280,460 B1 | 8/2001 | Bolduc |
| 6,290,711 B1 | 9/2001 | Caspari |
| 6,319,263 B1 | 11/2001 | Levinson |
| 6,322,112 B1 | 11/2001 | Duncan |
| 6,332,889 B1 | 12/2001 | Sancoff |
| 6,398,795 B1 | 6/2002 | McAlister |
| 6,425,900 B1 | 7/2002 | Knodel |
| 6,428,562 B2 | 8/2002 | Bonutti |
| 6,436,107 B1 | 8/2002 | Wang |
| 6,461,355 B2 | 10/2002 | Svejkovsky |
| 6,482,235 B1 | 11/2002 | Lambrecht |
| 6,488,691 B1 | 12/2002 | Carroll |
| 6,491,707 B2 | 12/2002 | Makower |
| 6,494,888 B1 | 12/2002 | Cruz |
| 6,500,195 B2 | 12/2002 | Bonutti |
| 6,506,190 B1 | 1/2003 | Walshe |
| 6,506,196 B1 | 1/2003 | Laufer |
| 6,517,569 B2 | 2/2003 | Mikus |
| 6,527,702 B2 | 3/2003 | Whalen |
| 6,527,794 B1 | 3/2003 | McDevitt |
| 6,530,932 B1 | 3/2003 | Swayze |
| 6,533,796 B1 | 3/2003 | Sauer |
| 6,547,725 B1 | 4/2003 | Paolitto |
| 6,551,328 B2 | 4/2003 | Kortenbach |
| 6,551,333 B2 | 4/2003 | Kuhns |
| 6,565,578 B1 | 5/2003 | Peifer |
| 6,569,187 B1 | 5/2003 | Bonutti |
| 6,572,626 B1 | 6/2003 | Knodel |
| 6,572,635 B1 | 6/2003 | Bonutti |
| 6,572,653 B1 | 6/2003 | Simonson |
| 6,592,609 B1 | 7/2003 | Bonutti |
| 6,596,013 B2 | 7/2003 | Yang |
| 6,626,913 B1 | 9/2003 | McKinnon |
| 6,626,916 B1 | 9/2003 | Yeung |
| 6,626,919 B1 | 9/2003 | Swanstrom |
| 6,629,534 B1 | 10/2003 | St. Goar |
| 6,641,592 B1 | 11/2003 | Sauer |
| 6,656,182 B1 | 12/2003 | Hayhurst |
| 6,660,023 B2 | 12/2003 | McDevitt |
| 6,663,589 B1 | 12/2003 | Halevy |
| 6,663,639 B1 | 12/2003 | Laufer |
| 6,699,263 B2 | 3/2004 | Cope |
| 6,706,047 B2 | 3/2004 | Trout |
| 6,709,493 B2 | 3/2004 | DeGuiseppi |
| 6,715,804 B2 | 4/2004 | Beers |
| 6,719,709 B2 | 4/2004 | Whalen |
| 6,730,112 B2 | 5/2004 | Levinson |
| 6,736,823 B2 | 5/2004 | Darois |
| 6,736,854 B2 | 5/2004 | Vadurro |
| 6,740,098 B2 | 5/2004 | Abrams |
| 6,767,037 B2 | 7/2004 | Wenstrom |
| 6,770,076 B2 | 8/2004 | Foerster |
| 6,773,438 B1 | 8/2004 | Knodel |
| 6,773,441 B1 | 8/2004 | Laufer |
| 6,790,213 B2 | 9/2004 | Cherok |
| 6,802,846 B2 | 10/2004 | Hauschild |
| 6,821,282 B2 | 11/2004 | Perry |
| 6,821,285 B2 | 11/2004 | Laufer |
| 6,821,291 B2 | 11/2004 | Bolea |
| 6,835,200 B2 | 12/2004 | Laufer |
| 6,905,475 B2 | 6/2005 | Hauschild |
| 6,908,473 B2 | 6/2005 | Skiba |
| 6,926,732 B2 | 8/2005 | Derus |
| 6,951,565 B2 | 10/2005 | Keane |
| 6,986,775 B2 | 1/2006 | Morales |
| 6,991,596 B2 | 1/2006 | Whalen |
| 6,991,647 B2 | 1/2006 | Jadhav |
| 6,997,940 B2 | 2/2006 | Bonutti |
| 7,001,327 B2 | 2/2006 | Whalen |
| 7,011,688 B2 | 3/2006 | Gryska |
| 7,015,253 B2 | 3/2006 | Escandon |
| 7,048,698 B2 | 5/2006 | Whalen |
| 7,048,747 B2 | 5/2006 | Arcia |
| 7,060,077 B2 | 6/2006 | Gordon |
| 7,081,126 B2 | 7/2006 | McDevitt |
| 7,083,638 B2 | 8/2006 | Foerster |
| 7,087,073 B2 | 8/2006 | Bonutti |
| 7,089,064 B2 | 8/2006 | Manker |
| 7,090,690 B2 | 8/2006 | Foerster |
| 7,093,601 B2 | 8/2006 | Manker |
| 7,096,301 B2 | 8/2006 | Beaudoin |
| 7,105,004 B2 | 9/2006 | DiCesare |
| 7,108,655 B2 | 9/2006 | Whalen |
| 7,141,038 B2 | 11/2006 | Whalen |
| 7,153,314 B2 | 12/2006 | Laufer |
| 7,179,225 B2 | 2/2007 | Shluzas |
| 7,226,558 B2 | 6/2007 | Nieman |
| 7,232,448 B2 | 6/2007 | Battles |
| 7,288,063 B2 | 10/2007 | Petros |
| 7,303,108 B2 | 12/2007 | Shelton |
| 7,320,701 B2 | 1/2008 | Haut |
| 7,322,974 B2 | 1/2008 | Swoyer |
| 7,334,822 B1 | 2/2008 | Hines |
| 7,340,300 B2 | 3/2008 | Christopherson |
| 7,399,304 B2 | 7/2008 | Gambale |
| 7,402,166 B2 | 7/2008 | Feigl |
| 7,416,554 B2 | 8/2008 | Lam |
| 7,553,317 B2 | 6/2009 | Weisenburgh |
| 7,608,108 B2 | 10/2009 | Bhatnagar |
| 7,645,286 B2 * | 1/2010 | Catanese et al. ............ 606/151 |
| 7,658,311 B2 | 2/2010 | Boudreaux |
| 7,674,275 B2 | 3/2010 | Martin |
| 7,727,248 B2 | 6/2010 | Smith |
| 2001/0044639 A1 | 11/2001 | Levinson |
| 2002/0095154 A1 | 7/2002 | Atkinson |
| 2002/0128684 A1 | 9/2002 | Foerster |
| 2002/0161382 A1 | 10/2002 | Neisz |
| 2002/0193809 A1 | 12/2002 | Meade |
| 2003/0109769 A1 | 6/2003 | Lowery |
| 2003/0191497 A1 | 10/2003 | Cope |
| 2003/0204195 A1 | 10/2003 | Keane |
| 2003/0236535 A1 | 12/2003 | Onuki |
| 2004/0030217 A1 | 2/2004 | Yeung |

(56) References Cited

U.S. PATENT DOCUMENTS

| | | | |
|---|---|---|---|
| 2004/0043052 A1 | 3/2004 | Hunter | |
| 2004/0078046 A1 | 4/2004 | Barzell | |
| 2004/0193191 A1 | 9/2004 | Starksen | |
| 2004/0193194 A1 | 9/2004 | Laufer | |
| 2004/0194790 A1 | 10/2004 | Laufer | |
| 2004/0243178 A1* | 12/2004 | Haut et al. | 606/232 |
| 2004/0243179 A1 | 12/2004 | Foerster | |
| 2004/0243180 A1 | 12/2004 | Donnelly | |
| 2004/0243227 A1 | 12/2004 | Starksen | |
| 2004/0260345 A1 | 12/2004 | Foerster | |
| 2005/0055087 A1 | 3/2005 | Starksen | |
| 2005/0065550 A1 | 3/2005 | Starksen | |
| 2005/0107811 A1 | 5/2005 | Starksen | |
| 2005/0107812 A1 | 5/2005 | Starksen | |
| 2005/0154401 A1 | 7/2005 | Weldon | |
| 2005/0177181 A1 | 8/2005 | Kagan | |
| 2005/0203344 A1 | 9/2005 | Orban | |
| 2005/0203550 A1 | 9/2005 | Laufer | |
| 2005/0216078 A1 | 9/2005 | Starksen | |
| 2005/0267405 A1 | 12/2005 | Shah | |
| 2005/0273138 A1 | 12/2005 | To | |
| 2006/0025750 A1 | 2/2006 | Starksen | |
| 2006/0025784 A1 | 2/2006 | Starksen | |
| 2006/0025789 A1 | 2/2006 | Laufer | |
| 2006/0025819 A1 | 2/2006 | Nobis | |
| 2006/0026750 A1 | 2/2006 | Ballance | |
| 2006/0030884 A1 | 2/2006 | Yeung | |
| 2006/0058817 A1 | 3/2006 | Starksen | |
| 2006/0089646 A1 | 4/2006 | Bonutti | |
| 2006/0167477 A1 | 7/2006 | Arcia | |
| 2006/0265042 A1 | 11/2006 | Catanese | |
| 2006/0282081 A1 | 12/2006 | Fanton | |
| 2007/0049929 A1 | 3/2007 | Catanese | |
| 2007/0049970 A1 | 3/2007 | Belef | |
| 2007/0060931 A1 | 3/2007 | Hamilton | |
| 2007/0088362 A1 | 4/2007 | Bonutti | |
| 2007/0112385 A1 | 5/2007 | Conlon | |
| 2007/0142846 A1 | 6/2007 | Catanese | |
| 2007/0173888 A1 | 7/2007 | Gertner | |
| 2007/0260259 A1 | 11/2007 | Fanton | |
| 2008/0009888 A1 | 1/2008 | Ewers | |
| 2008/0021445 A1 | 1/2008 | Elmouelhi | |
| 2008/0033488 A1 | 2/2008 | Catanese | |
| 2008/0039894 A1 | 2/2008 | Catanese | |
| 2008/0045978 A1 | 2/2008 | Kuhns | |
| 2008/0058710 A1 | 3/2008 | Wilk | |
| 2008/0065120 A1 | 3/2008 | Zannis | |
| 2008/0082113 A1 | 4/2008 | Bishop | |
| 2008/0086172 A1 | 4/2008 | Martin | |
| 2008/0091220 A1 | 4/2008 | Chu | |
| 2008/0091237 A1 | 4/2008 | Schwartz | |
| 2008/0119874 A1 | 5/2008 | Merves | |
| 2008/0154378 A1 | 6/2008 | Pelo | |
| 2008/0195145 A1 | 8/2008 | Bonutti | |
| 2008/0208220 A1 | 8/2008 | Shiono | |
| 2010/0010631 A1 | 1/2010 | Otte | |
| 2010/0114162 A1 | 5/2010 | Bojarski | |
| 2010/0286106 A1 | 11/2010 | Gat | |
| 2010/0286679 A1 | 11/2010 | Hoey | |

FOREIGN PATENT DOCUMENTS

| | | | |
|---|---|---|---|
| EP | 0632999 | A1 | 1/1995 |
| EP | 0464480 | | 3/1995 |
| EP | 1082941 | | 3/2005 |
| EP | 1016377 | | 4/2006 |
| EP | 1006909 | | 1/2007 |
| EP | 1852071 | A2 | 11/2007 |
| EP | 1670361 | | 4/2008 |
| EP | 1331886 | | 12/2008 |
| EP | 1884198 | | 3/2010 |
| EP | 1884199 | | 1/2011 |
| FR | 2750031 | A1 | 12/1997 |
| JP | 5836559 | A | 3/1983 |
| JP | 09122134 | A | 5/1997 |
| JP | 2004344427 | A | 12/2004 |
| RU | 2112571 | C1 | 6/1998 |
| RU | 2128012 | C1 | 3/1999 |
| RU | 2221501 | C2 | 1/2004 |
| SU | 825094 | A1 | 4/1981 |
| SU | 2062121 | C1 | 10/1989 |
| WO | WO-9210142 | | 6/1992 |
| WO | WO-9304727 | | 3/1993 |
| WO | WO-9315664 | | 8/1993 |
| WO | WO-0230335 | | 4/2002 |
| WO | WO-03039334 | | 5/2003 |
| WO | WO-03077772 | | 9/2003 |
| WO | WO-2004017845 | | 3/2004 |
| WO | WO-2004019787 | | 3/2004 |
| WO | WO-2004030569 | | 4/2004 |
| WO | WO-2004103189 | | 12/2004 |
| WO | WO-2007053516 | | 5/2007 |
| WO | WO-2007064906 | | 6/2007 |
| WO | WO-2008006084 | | 1/2008 |
| WO | WO-2008043044 | | 4/2008 |
| WO | WO-2008043917 | | 4/2008 |
| WO | WO-2009009617 | | 1/2009 |
| WO | WO-2010011832 | | 1/2010 |

OTHER PUBLICATIONS

Berges, Richard, "Alternative Minimalinvasive Therapien Beim Benignen Prostatasyndrom ", medizin, Jg, 104 heft 37, (Sep. 2007), 12 pgs.

Borzhievski, "Tactics of the Surgical Treatment of Patients With Prostatic Adenoma and Acute Urinary Retention", Urologia Nefrol (Mosk), (1), (1987), 39-43.

Hartung, Rudolf, "Instrumentelle Therapie der benegnen Prostatahyperplasie", Medizin, Deutsches Arzteblatt 97, Heft 15, (Apr. 2000), 8 pgs.

Hofner, Klaus, "Operative Therapie des benignen Prostatasyndroms", Medizin, Dtsch Arztebl, 194(36), (2007), 6 pgs.

Hubmann, R, "Geschichte der transurethralen Prostataeingriffe", Geschichte der Medizin, Urologe (B), 40, (2000), 152-160.

"International Application Serial No. PCT/US2007/74019, International Search Report mailed on Jul. 25, 2008", 1 pg.

Jonas, U, "Benigne Prostatahyperplasie", Der Urologe, 45, (2006), 134-144.

Kruck, S, "Aktuelle Therapiemoglichkeiten des Benignen Prostata-Syndroms", J Urol Urogynakol 209,16 (1), (2009), 19-22.

Miyake, Osamu, "Medical Examination and Treatment for BPH", Pharma Med, vol. 22, No. 3, (2004), 97-103.

Reich, O, "Benignes Prostatasyndrom (BPS)", Der Urologe, A Issue, vol. 45, No. 6, (Jun. 2006), 769-782.

Schauer, P, "New applications for endoscopy: the emerging field of endoluminal and transgastric bariatric surgery", Surgical Endoscopy, (Apr. 24, 2006), 10 pgs.

Sharp, Howard T, "Instruments and Methods—The 4-S Modification of the Roeder Knot: How to Tie It", Obstetrics & Gynecology, vol. 90, No. 6, (Dec. 1, 1997), 1004-1006.

Takashi, Daito, "Low-Invasive Treatment for BPH", Medico vol. 34, No. 10, 366-369.

Teruhisa, Ohashi, "Urinary Dysfunction by Lower Urinary Tract Obstruction in Male", Pharma Medica, vol. 8, No. 8, 35-39.

Tomohiko, Koyanagi, "Surgery View of 21st Century", Urological Surgery, vol. 84, No. 1, 47-53.

Trapeznikov, "New Technologies in the Treatment of Benign Prostatic Hyperplasia", Urologia Nefrol(Mosk), (4), (Jul.-Aug. 1996), 41-47.

Yeung, Jeff, "Treating Urinary Stress Incontinence Without Incision with Endoscopic Suture Anchor & Approximating Device", Aleeva Medical, Inc, (2007), 31 pgs.

* cited by examiner

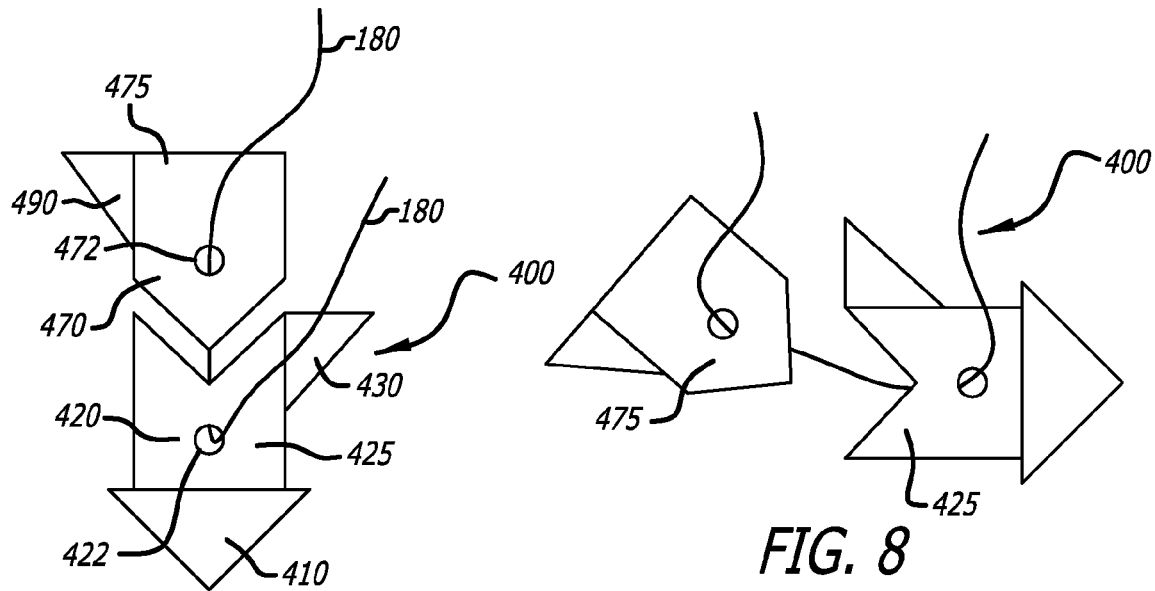
FIG. 7
FIG. 8
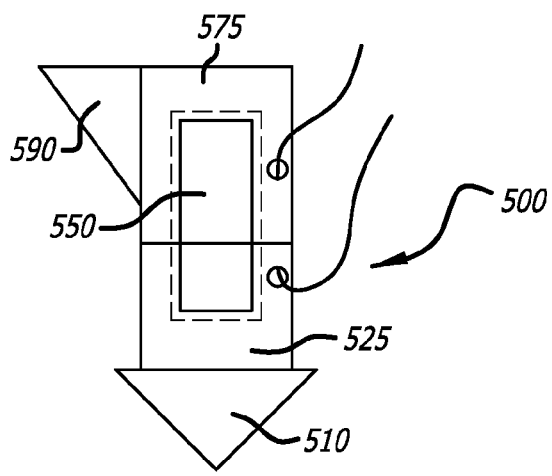
FIG. 9
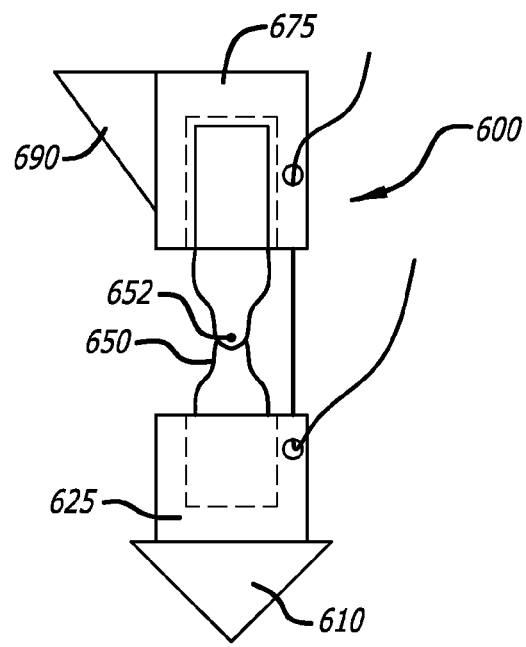
FIG. 10

SUTURE ANCHORING DEVICES AND METHODS FOR USE

CROSS-REFERENCE TO RELATED APPLICATIONS

This application is a continuation-in-part of copending U.S. patent application Ser. No. 12/791,805, entitled Integrated Handle Assembly for Anchor Delivery System, filed on Jun. 1, 2010, which is a continuation-in-part of U.S. patent application Ser. No. 11/492,690, now U.S. Pat. No. 7,896,891, entitled Apparatus and Method for Manipulating or Retracting Tissue and Anatomical Structure, filed on Jul. 24, 2006, which is a continuation-in-part of U.S. patent application Ser. No. 11/318,246, now U.S. Pat. No. 7,645,286, entitled Devices, Systems and Methods for Retracting, Lifting, Compressing, Supporting or Repositioning Tissues or Anatomical Structures, filed on Dec. 22, 2005, which is a continuation-in-part of U.S. patent application Ser. No. 11/134,870, now U.S. Pat. No. 7,758,594, entitled Devices, Systems and Methods for Treating Benign Prostatic Hyperplasia and Other Conditions, filed on May 20, 2005, the entire disclosures of which are expressly incorporated herein by reference.

This application claims priority to and the benefit of U.S. Provisional Application No. 61/707,752 filed Sep. 28, 2012 entitled Suture Anchoring Devices and Methods for Use, which application is incorporated herein by reference in its entirety.

BACKGROUND OF THE INVENTION

The present invention relates to a surgical implant for attachment of soft tissue to bone, an insertion tool for anchoring suture anchors to bone, and a method for anchoring a suture anchor to bone.

It is often necessary to attach soft tissue to bone, for example, to attach ligament tissue to bone tissue. Loss of integrity in bone tissue, for example, a ligament of a human rotator cuff, as well as recurrent dislocation of the shoulder, may result in abnormal kinematics of the shoulder. This may cause progressive weakness of the shoulder and, in some circumstances, severe dysfunction of the shoulder and progressive degenerative joint changes. Accordingly, procedures have been developed to repair, for example, the rotator cuff, to prevent debilitating loss of function and to restore more physiologic biomechanics. However, these conventional procedures may require invasive surgical procedures, which may lead to increased complications and increased morbidity.

Many of the early suture anchors were operable to be screwed into the bone. However, to properly secure such an anchor, the bone had to be first prepared by a separate tapping step (i.e., a pre-drilling step). In an effort to eliminate the initial tapping step, push-in type anchors were developed. The effectiveness of push-in type anchors may be measured by their ability to reliably set in all bone types, the size of the anchor, and the effectiveness of insertion tools for protecting suture threads while inserting the anchors into bone.

With respect to push-in type suture anchors, the insertion tool, the suture implant, and the method of insertion should act to consistently and reliably set the implant in a variety of bone types. For this purpose, the implant should be designed as small as possible to limit the amount of foreign substance in the body, and should have features configured to consistently set the anchor into bone.

Due to the limitations of the conventional suture anchors, delivery instruments, and methods described above, a need exists for a simple, strong, and reliable suture anchor, as well as a technique for fixating suture to bone.

Furthermore, a need exists for a push-in type suture anchor and delivery instrument that protects the sutures during insertion of the anchor into bone.

Effective tissue anchors require a contradictory combination of small size for ease of delivery and large size for substantial tissue purchase.

Other applications for tissue anchors include manipulating or retracting tissues and anatomical or other structures within the body of human or animal subjects for the purpose of treating diseases or disorders. One example of a condition where it is desirable to lift, compress or otherwise remove a pathologically enlarged tissue is Benign Prostatic Hyperplasia (BPH).

The present disclosure addresses these and other needs.

BRIEF SUMMARY OF THE INVENTION

Embodiments of the invention include a suture anchor comprising a distal portion configured to penetrate tissue, a proximal portion comprising a wing, and a body portion comprising a telescoping portion configured to extend upon placement within tissue.

Embodiments of the invention include a suture anchor comprising a distal portion configured to penetrate tissue, a proximal portion comprising a wing, and a body portion comprising a plurality of nested segments configured to separate and increase the effective volume of the suture anchor upon placement within tissue.

Embodiments of the invention include a suture anchor comprising a distal portion configured to penetrate tissue, a proximal portion comprising a wing, and a body portion comprising an expandable portion configured to increase the effective volume of the suture anchor upon placement within tissue.

Embodiments of the invention include a method of placing a suture anchor comprising driving the suture anchor having an asymmetric cross-section through a tissue surface and into a tissue volume, wherein an asymmetric hole is formed in the tissue surface, rotating the suture anchor about a longitudinal axis of the suture anchor, pivoting the suture anchor such that its longitudinal axis is comparatively less perpendicular to the tissue surface than when the suture anchor was driven into tissue, and backfilling the hole with a material capable of providing a physical barrier to the suture anchor. In some embodiments the material is a plug and in some embodiments the material is a flowable substance.

Embodiment of the invention include a method of treating a prostate including penetrating the prostatic capsule with a suture anchor configured to increase its effective volume upon placement in tissue.

Other features and advantages of the present disclosure will become apparent from the following detailed description, taken in conjunction with the accompanying drawings, which illustrate, by way of example, the principles of the invention.

BRIEF DESCRIPTION OF SEVERAL VIEWS OF THE DRAWINGS

FIGS. 7 and 8 illustrate nesting suture anchors according to embodiments of the invention.

FIG. 9 illustrates a suture anchor with telescoping segments according to embodiments of the invention.

FIG. 10 illustrates an alternative embodiment of a telescoping suture anchor according to embodiments of the invention.

DETAILED DESCRIPTION OF THE INVENTION

Before the present devices and methods are described, it is to be understood that this invention is not limited to particular embodiments described, as such may vary from the specific embodiments. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Short summaries of certain terms are presented in the description of the invention. Each term is further explained and exemplified throughout the description, figures, and examples. Any interpretation of the terms in this description should take into account the full description, figures, and examples presented herein.

Figure 1:
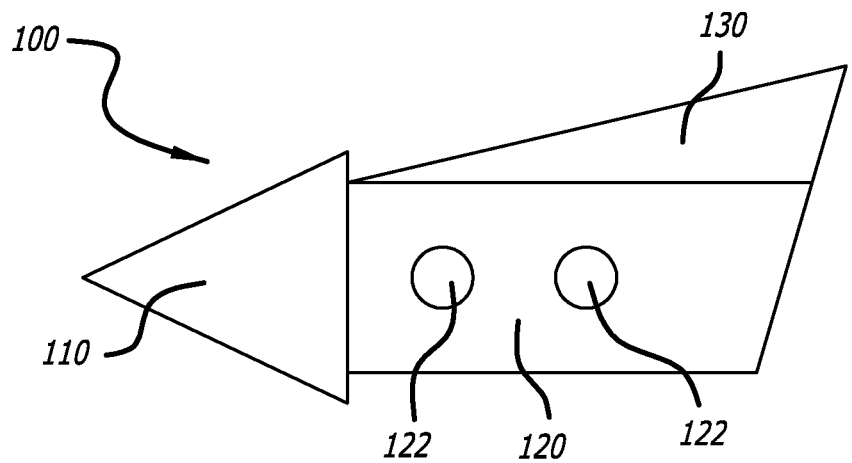
FIGS. 1-5 depict suture anchors of the prior art and methods of insertion.
Figure 2:
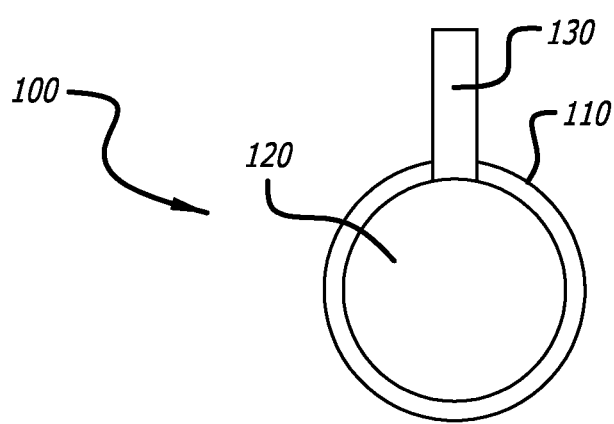

FIG. 1 illustrates a side view of a suture anchor of the prior art and FIG. 2 illustrates a back view of the same prior art suture anchor. Anchor 100 includes a conical distal portion 110, body 120, and wing 130. Conical distal portion 110 is configured to penetrate tissue and in particular bone tissue. Body 120 includes holes 122 through which suture may be threaded. Wing 130 is connected to body 120. FIG. 2 illustrates the back view of suture anchor 108 and depicts the relationship among fin 130, body 120, and conical distal portion 110.

Figure 3:
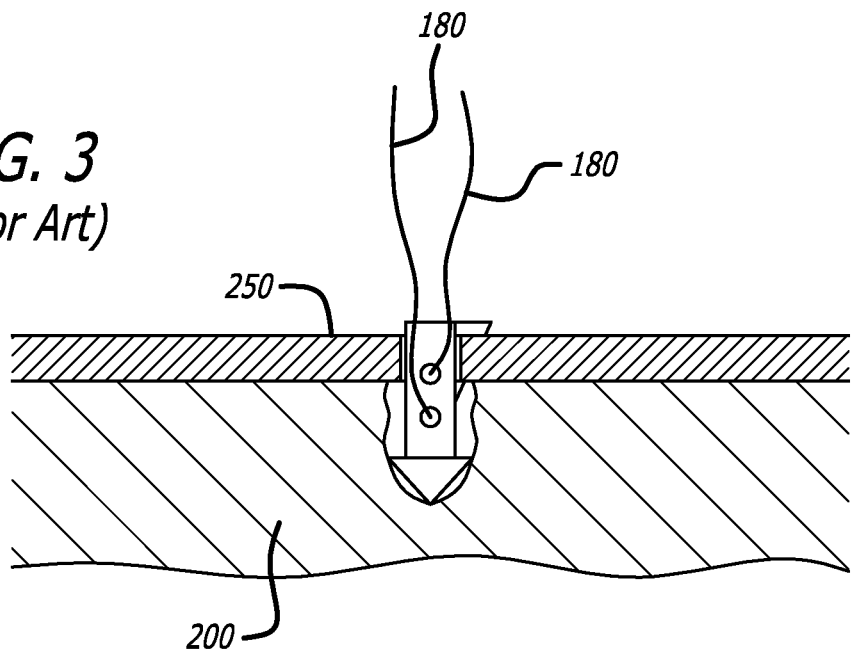

FIG. 3 illustrates a prior art method for inserting suture anchor 100 into tissue and in particular bone tissue. FIG. 3 depicts sutures 180 connected through holes 122. Suture anchor 100 is depicted as being driven through cortical layer 250 of bone tissue and into the comparatively softer cancellous layer 200 of bone tissue. The conical distal portion of the suture anchor facilitates placement of the suture anchor.

Figure 4:
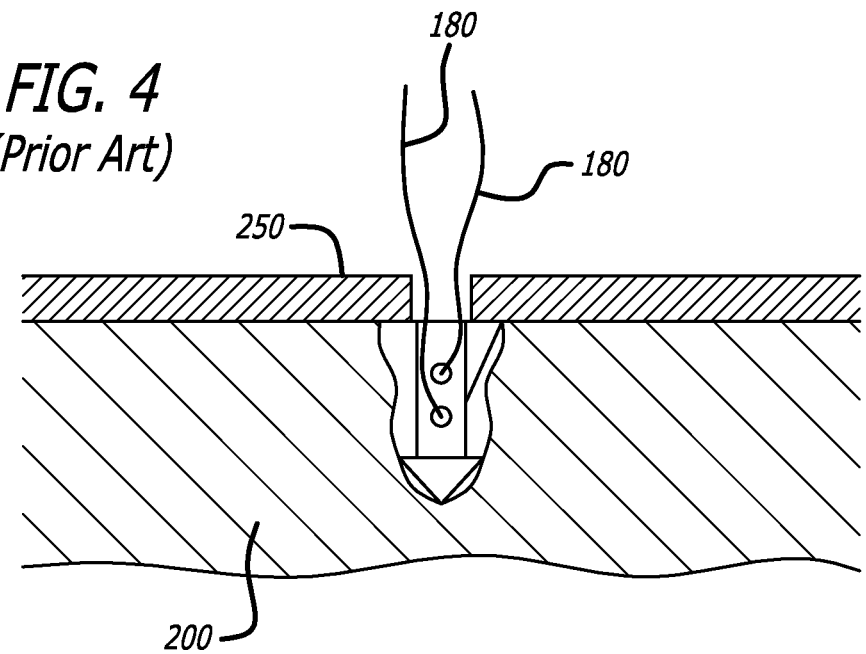
Figure 5:
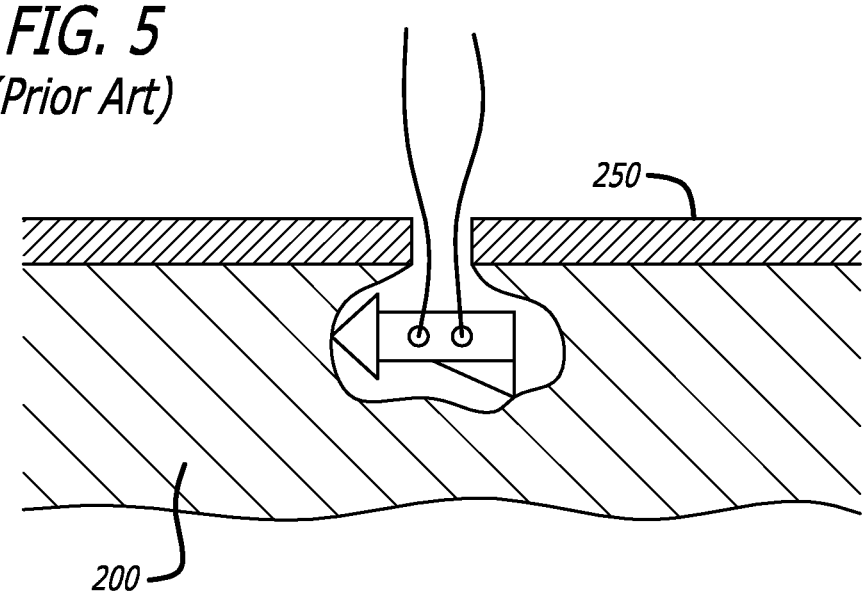

FIG. 4 illustrates a further step in the prior art method of inserting suture anchor 100 into bone tissue in which the proximal end of the suture anchor has penetrated beyond the cortical layer 250 of bone tissue and is completely within the cancellous layer 200 of bone tissue. FIG. 5 illustrates a further step in the method of placing prior art suture anchors in which the anchor pivots with respects to the axis of its entry into bone tissue after having been rotated such that the wing is positioned in such a way as to prevent the suture anchor from backing out through the hole left in the cortical layer of bone tissue.

When the suture anchor is advanced through the cortical layer of bone, the wing of the anchor leaves a radial slot through the surface of the cortical layer of bone. The final position of the suture anchor within the bone tissue relies on friction and the three-step installation (that is, the axial penetration of the anchor into tissue, rotation of the anchor about its longitudinal axis to misalign the wing with the radial slot in the cortical layer of bone, and the pivoting or toggling of the anchor to increase its "footprint" within the cancellous layer of bone such that it is wider than the entry hole in the cortical layer) to maintain the anchor body parallel relative to the cortical layer.

According to certain embodiments of the present invention, the positioning and permanence of the suture anchor is improved such that the suture anchor will stay in the final position and not back out of the bone tissue.

Figure 6:
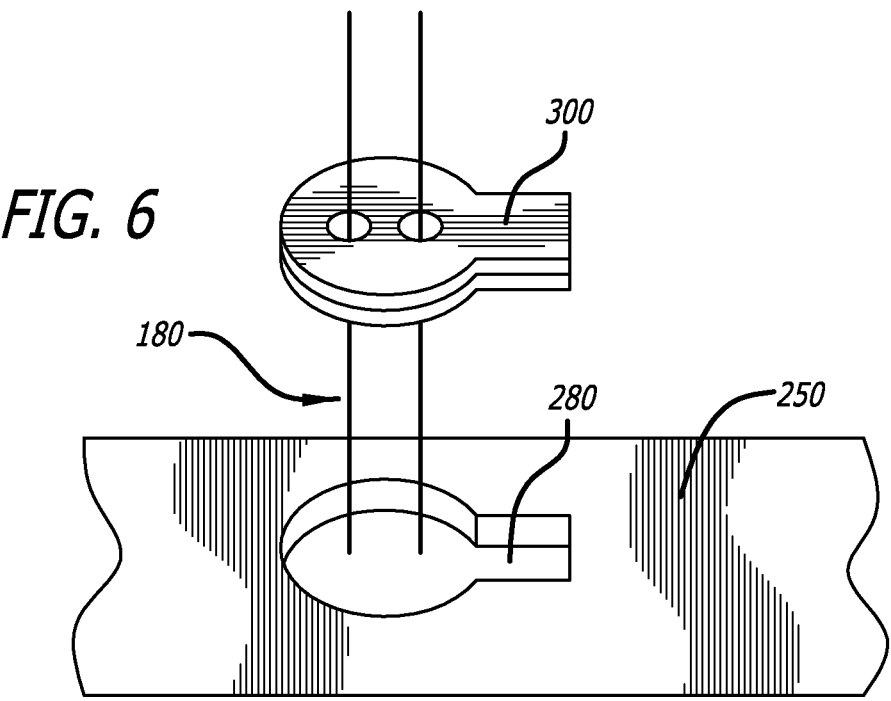
FIG. 6 illustrates a method for improving the placement of suture anchors and elements related to such improvements, according to embodiments of the invention.

FIG. 6 illustrates a perspective view of cortical bone layer 250 after a suture anchor has been driven through cortical bone layer 250. FIG. 6 depicts the surface of cortical bone layer 250 as including keyhole 280. Keyhole 280 roughly corresponds to the cross section of the suture anchor, including the wing of the suture anchor (similar to the back view of the suture anchor depicted in FIG. 2). In prior art suture anchors, the suture anchor is rotated and pivoted to prevent it from backing out of keyhole 280.

According to certain embodiments of the present invention, after deploying the suture anchor into its position within the cancellous bone, and optionally after rotating and pivoting the suture anchor, keyhole 280 is backfilled with a biocompatible substance. The biocompatible substance is capable of swelling, hardening, or otherwise providing an additional mechanical barrier that helps prevent the suture anchor from backing out of keyhole 280. Certain bone cements, such as, but not limited to, polymethyl methacrylate, can be used to backfill keyhole 280.

In some embodiments, the space in the cancellous bone around the suture implant may also be filled with the biocompatible substance that provide this additional mechanical barrier. In some embodiments, it may be advantageous to apply the biocompatible substance prior to rotating the suture anchor and/or prior to pivoting the suture anchor. In such embodiments, applying the biocompatible substance prior to rotating and/or pivoting the suture anchor can help spread, mix, or commingle the biocompatible substance with the suture anchor, in the space around the suture anchor, and with the cancellous bone tissue near the suture anchor.

In some embodiments, it may be advantageous to apply the biocompatible substance after the suture anchor has been rotated and pivoted into a desired position. In such embodiments, applying the biocompatible substance after the suture anchor is in its desired position may allow for substantially complete backfilling of keyhole 280 and/or the space around the suture anchor.

According to certain embodiments, the biocompatible substance is capable of flowing or has a sufficiently low viscosity such that it can be applied to occupy the space in keyhole 280 and/or the space around the suture anchor. Liquids and gels, including two-part liquids and gels that thicken and or cure when mixed, may have suitable flow characteristics.

The biocompatible substance filling the space around the suture anchor and in the keyhole provides additional strength to the suture anchor and assurance that it will not back out. Embodiments of the invention improve on current suture anchor technologies that rely on friction and/or a narrow installation pathway. If installation of the suture anchor is difficult and the space needed to rotate the suture anchor becomes larger than desired, the prior art suture anchor alone may not have a sufficient footprint for the suture anchor to remain in place. Further, the quality of the tissue into which the suture anchor is implanted may be low and may not be sufficiently strong to hold the anchor in place. The biocompatible substance can provide additional strength in both of these situations.

The biocompatible substance may be delivered with the same tool that helps insert and install the suture anchor or it may be delivered with a separate tool.

FIG. 6 depicts plug 300, which has a shape similar to that of keyhole 280 according to certain embodiments. Plug 300 includes holes through which suture 180 may be threaded. Plug 300 may be used to fill some or all of keyhole 280 after the suture anchor has been placed in the desired position. In certain embodiments, the biocompatible substance may be used to further seal plug 300 into place. In some embodiments, the biocompatible substance is applied to the area around the suture anchor prior to the plug 300 being placed within the keyhole 280. In certain embodiments, the biocompatible substance is applied to plug 300 after it has been placed within keyhole 280.

Other embodiments of the invention further improve upon conventional suture anchors.

FIG. 7 illustrates an embodiment of the invention in which the suture anchor includes at least two nested anchor segments. FIG. 7 depicts suture anchor 400 as including two anchor segments 425 and 475. Distal anchor segment 425 includes conical distal portion 410, distal body 420, and distal wing 430. Distal anchor segment 425 also includes hole 422 through which suture 180 is threaded. Proximal anchor segment 475 includes proximal body 470 and proximal wing 490. Proximal anchor segment 475 includes hole 472 through which suture 180 is threaded. Distal anchor segment 425 and proximal anchor segment 475 include complementary ends configured to allow the anchor segments to nest together to form a substantially rigid suture anchor. When the anchor segments are nested together, suture anchor 400 can be driven into tissue more easily than when the anchor segments are separated. FIG. 7 depicts one nesting configuration in which the proximal anchor segment 475 has a pointed distal end and distal anchor segment 425 has an inverted pointed shape on its proximal end. It is understood that other complementary shapes for the nesting ends of the anchor segments are within the scope of the invention.

FIG. 8 illustrates a nested suture anchor in which the nested segments are separated. When anchor segments 425 and 475 are separated, the footprint of the suture anchor is larger than when they are nested and such larger footprint provides improved anchoring within the tissue as compared to conventional anchors.

According to embodiments of the invention, the tissue anchor includes a plurality of segments, which are stacked in an in-line configuration for delivery to a site within the body. Each segment is connected to a single connecting member. On delivery into the target site the connecting member is tensioned and the segments separate. The separate segments create a volume that is commingled with local tissue and resists pulling through the delivery hole. Alternative versions of this embodiment include a nesting design of the individual segments, separate connecting members, or separate filaments of the same connecting member.

FIG. 9 illustrates a suture anchor with telescoping segments. Distal segment 525 and proximal segment 575 are depicted in FIG. 9 in a collapsed configuration in which central segment 550 is substantially within an interior space of each of distal segment 525 and proximal segment 575. Central segment 550 is configured to allow distal segment 525 and proximal segment 575 to extend to a greater length. The telescoping segments may be spring biased to extend when under tension from the sutures. Further, the telescoping segments may be drawn into an extended configuration when under tension from the sutures.

In another embodiment, connecting members or separate filaments of the same connecting member are individually attached to each telescoping segment of the suture anchor. The attachment points for the filaments or connecting members are positioned on the telescoping segments such that tension in the filaments exerts a length-expanding force on the telescoping elements.

FIG. 10 illustrates an alternative embodiment of a telescoping suture anchor. Suture anchor 600 includes proximal segment 675 and distal segment 625. Central pivoting connector 650 includes pivot point 652 about which the two segments can pivot. The combination of a central pivoting connector and the telescoping segments provides suture anchor 600 with a larger footprint within tissue when implanted.

In the telescoping environments, a locking mechanism can help maintain the extended configuration of the telescoped segments.

In certain embodiments presented herein, the comparatively short length of the tissue anchor facilitates delivery through curved trajectories. Upon delivery into tissue, the suture anchors expand in effective length and/or volume. This provides a large surface area that helps prevent the anchor from returning through the delivery hole.

Figure 11:
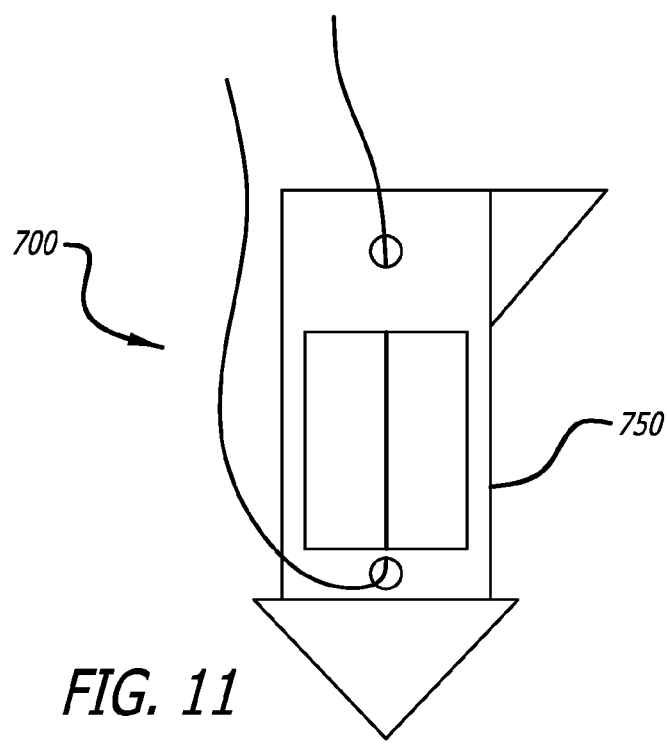
FIGS. 11 and 12 illustrate an embodiment in which the suture anchor includes an expanding element according to embodiments of the invention.
Figure 12:
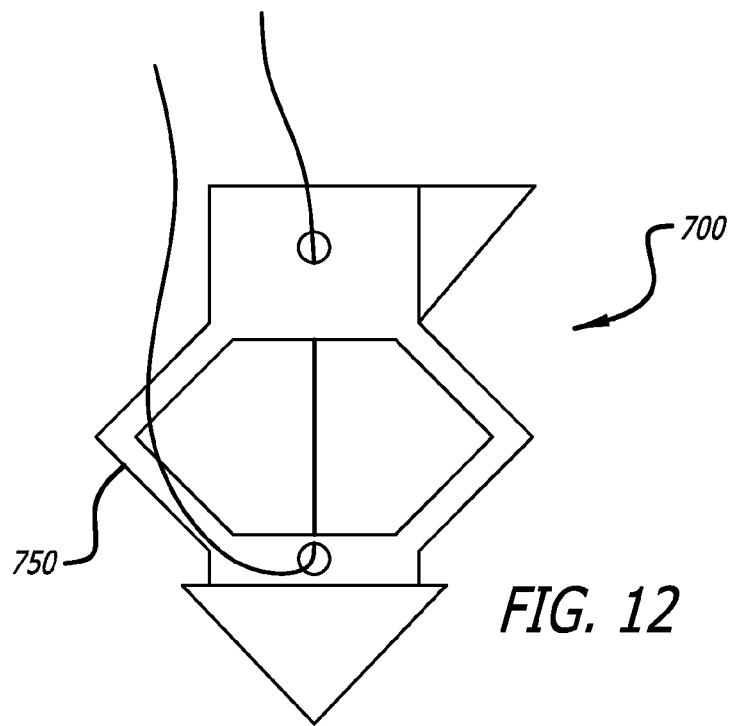

FIGS. 11 and 12 illustrate an embodiment in which the suture anchor includes an expanding element. Suture anchor 700 includes flexible legs 750 that are positioned about a cutout in the body of suture anchor 700. During delivery, a rod or similar device would be inserted into the anchor. To set the anchor, the rod would be removed and tension would be applied to the suture, collapsing the flexible legs. In this configuration, the suture anchor expands in effective volume and helps prevent the anchor from returning through the delivery hole.

Suture anchors disclosed herein are suitable for use in various parts of the anatomy. For example, such suture anchors can be used to displace or compress one or more lobes of the prostates gland to reduce or eliminate symptoms of benign prostatic hyperplasia.

Figure 13A:
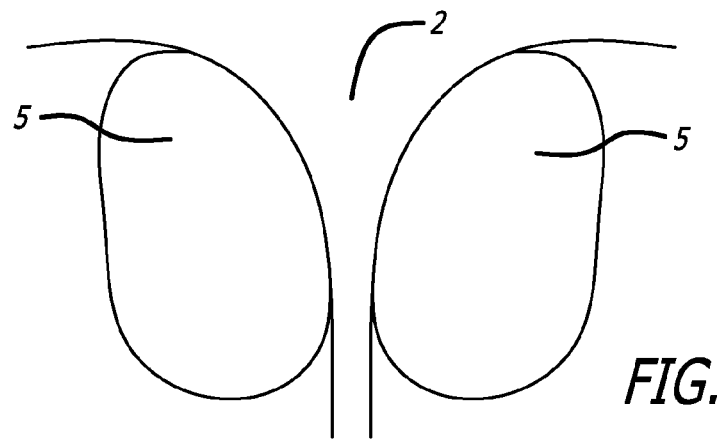
FIGS. 13A and 13B illustrate views of a narrowed and a widened prostatic urethra, respectively.
Figure 13B:
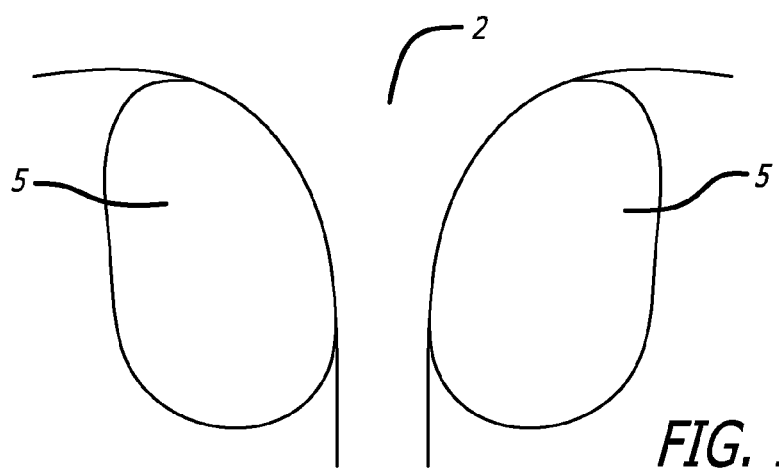

FIGS. 13A and 13B depict urethra 2 and prostatic lobes 5. In FIG. 13A, lobes 5 are narrowing the width of urethra 2, and such narrowing produces symptoms such as urinary hesitancy, frequent urination, painful urination, increased risk of urinary tract infections, and urinary retention. FIG. 13B illustrates the prostatic lobes of FIG. 13A after the narrowing of the urethra has been reduced. Suture anchors according to embodiments described herein can be used to displace or compress the prostatic lobes and/or reduce the narrowing of the urethra.

Figure 14:
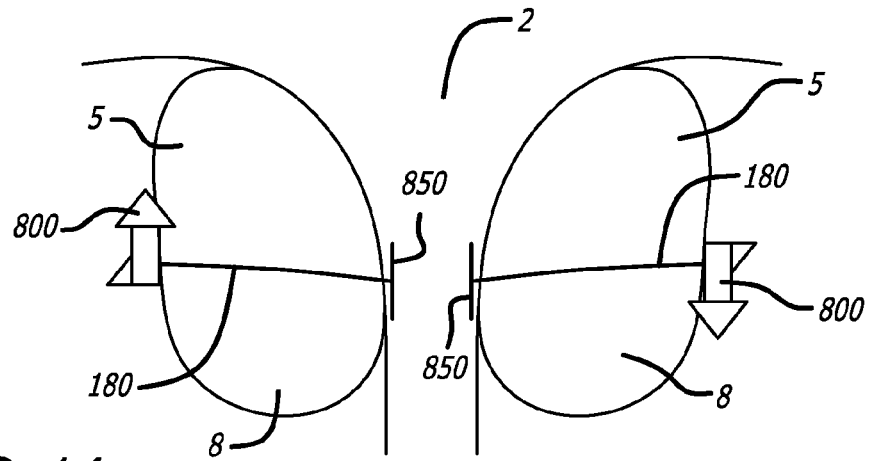
FIG. 14 illustrates a method for reducing narrowing in a prostatic urethra using suture anchors according to embodiments of the invention.

FIG. 14 illustrates a method for reducing narrowing in urethra 2 using suture anchors 800 according to embodiments described herein. In FIG. 14, a single suture anchor 800 has been deployed such that the suture anchor 800 is position on the outer surface of the prostatic capsule 8, which is a membrane that surrounds and encloses the prostate gland. Suture anchor 800 can be passed through prostatic lobe 5 and through prostatic capsule 8 to be deployed. Suture anchor 800 can be passed through a pre-existing delivery track made by a penetrating device, such as a trocar or a needle. Or, suture anchor 800 can be carried by the penetrating device to the outside of prostatic capsule 8. For example, the anchor can be carried within a hollow needle, can ride on the outside of a trocar, or can be delivered by equivalent methods. In certain embodiments, suture anchor 800 is sufficiently sharp such that it can be the penetrating tip of a penetrating delivery device. That is, suture anchor 800 can ride towards the end of a pusher, and the pusher can be retracted when the suture anchor reaches the outside of prostatic capsule 8. Suture anchor 800 is attached to suture 180, and suture 180 is carried along with suture anchor 800 during deployment. Suture 180 traverses prostatic lobe and terminates at urethral tab 850. Urethral tab 850 may be attached to suture 180 prior to or after suture anchor 800 is deployed to the outer surface of prostatic capsule 8.

Figure 15:
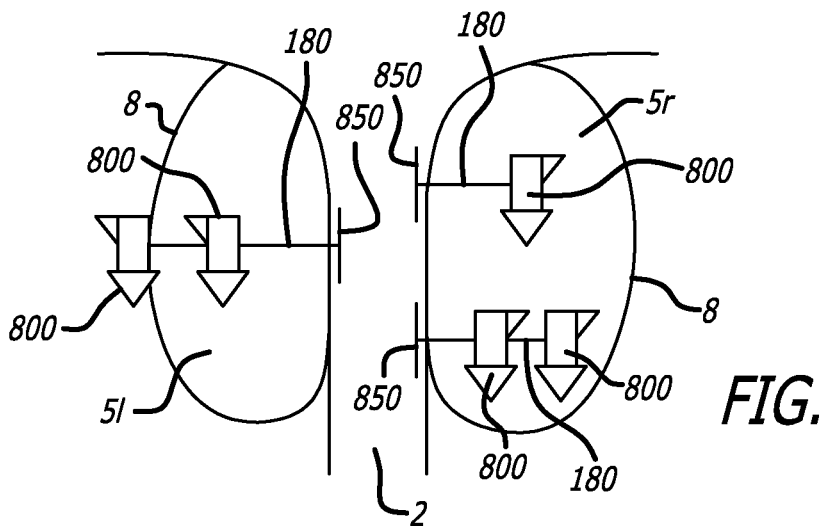
FIG. 15 illustrates another method for reducing narrowing in a prostatic urethra using suture anchors according to embodiments of the invention.

FIG. 15 illustrates another method for reducing narrowing in urethra 2 using suture anchors 800 according to embodiments described herein. The right prostatic lobe 5r is depicted with two different anchoring methods. In one method, a single suture anchor 800 is deployed within the prostatic lobe rather than outside the prostatic capsule as depicted in FIG. 14. Like the embodiments depicted in FIG. 14, suture anchor 800 is connected to urethral tab 850 via suture 180. Suture anchor 800 can be passed through a pre-existing delivery track made by a penetrating device, such as a trocar or a needle. Or, suture anchor 800 can be carried by the penetrating device to a position within prostatic lobe 5r. For example, the anchor can be carried within a hollow needle, can ride on the outside of a trocar, or can be delivered by equivalent methods. In certain embodiments, suture anchor 800 is sufficiently sharp such that it can be the penetrating tip of a penetrating delivery device. That is, suture anchor 800 can ride towards the end of a pusher, and the pusher can be retracted when the suture anchor reaches delivery position within prostatic lobe 5.

FIG. 15 illustrates embodiments in which more than one suture anchor 800 is connected to a single urethral tab 850. In one embodiment, two suture anchors 800 are deployed within prostatic lobe 5r. The suture anchors 800 can be deployed using the needle or trocar methods, or their equivalents, described herein. Similarly, the suture anchors 800 can be delivered using a pre-existing penetration track or using a pusher having a suture anchor 800 as its penetration tip. Suture 180 connects both suture anchors 800 to urethral tab 850 and to each other.

While FIG. 15 depicts suture anchors 800 in the same plane, of course prostatic lobe 5r is a three-dimensional structure and suture anchors 800 need not be in the same plane. Further, each suture anchor 800 maybe connected via separate sutures 180 to a single urethral tab 850.

FIG. 15 illustrates another embodiment in which multiple suture anchors 800 are deployed to reduce urethral narrowing. In this embodiment, one suture anchor 800 is deployed to the outer surface of prostatic capsule 8 and one suture anchor 800 is deployed within prostatic lobe 5l. Suture 180 connects suture anchors 800 to urethral tab 850 and each other.

Figure 16:
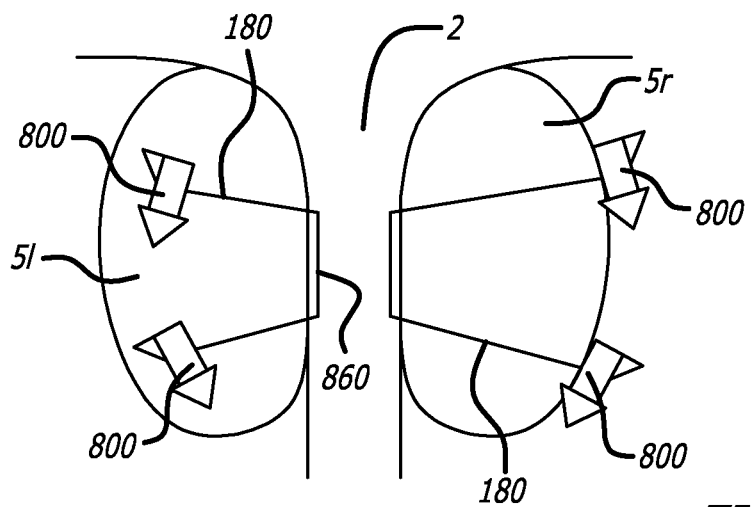
FIG. 16 illustrates multiple suture anchors deployed within the prostatic lobe or on the outer surface of the prostatic capsule of a prostatic lobe according to embodiments of the invention.

FIG. 16 illustrates multiple suture anchors 800 deployed within the prostatic lobe 5l or on the outer surface of the prostatic capsule 8 of prostatic lobe 5r. The multiple anchors are connected by suture 180, and in these embodiments suture 180 passes across the urethral side of the prostatic lobes 5r and 5l. Similar to the embodiments in FIG. 15, suture anchors 800 may be placed within the prostatic lobe or on the outer surface of the prostatic capsule using a penetrating member. In certain embodiments, suture 180 is connected to both anchors prior to deployment. Suture 180 may be fixed to the first suture anchor 800 that is deployed and coupled to the second suture anchor 800 such that suture 180 may be tensioned. As with other embodiments disclosed herein, suture 180 can be tensioned using the delivery device. Further, an optional suture lock 860 can be used to lock the tensioned suture in place. As with other embodiments disclosed herein, a cutting device may be used to cut the free end of the suture after it has been tensioned and secured to a urethral tab or a suture lock. Further, a knot can be used in addition to or instead of a suture lock of urethral tab.

According to certain embodiments, suture lock 860 can be a ferrule, which can be crimped either on the suture on the urethral side of the prostatic lobe or at the joint of the urethra and suture. In the case where the ferrule is crimped to the suture on the urethral side of the prostatic lobe, the ferrule can act as a urethral tab.

Figure 17:
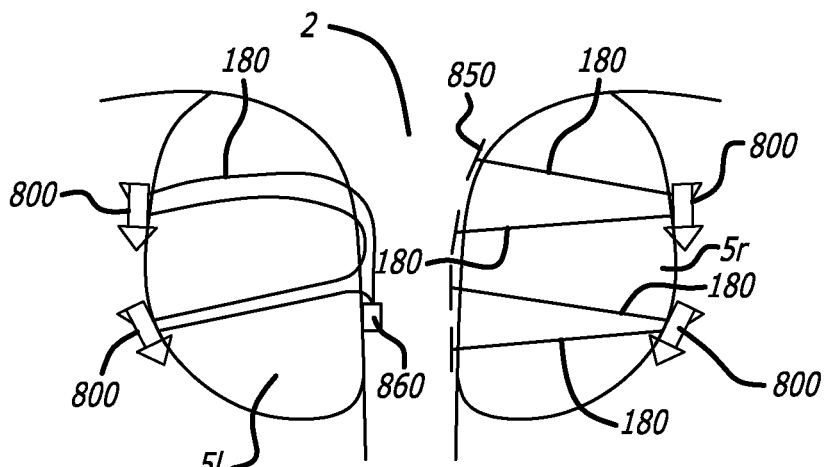
FIG. 17 illustrates further alternate embodiments in which multiple suture paths through a prostatic lobe are used to reduce the narrowing of the prostatic urethra according to embodiments of the invention.

FIG. 17 depicts further alternate embodiments in which multiple suture paths through a prostatic lobe are used to reduce the narrowing of the urethra. Prostatic lobe 5r depicts two suture anchors 800 that each have two sutures 180 extending from them to connect with a total of four urethral tabs on the urethral side of the prostatic lobe 5r. Such multiple suture strands can be tensioned and cut as described herein or using equivalent methods. Of course, the method is not limited to two suture strands per suture anchor. FIG. 17 also depicts an embodiment in a single suture 180 traverses prostatic lobe 5l multiple times before being secured on the urethral side of prostatic lobe 5l. Suture 180 can be secured using the methods and devices disclosed herein, such as knots, ferrules, tab, or their equivalents.

Figure 18:
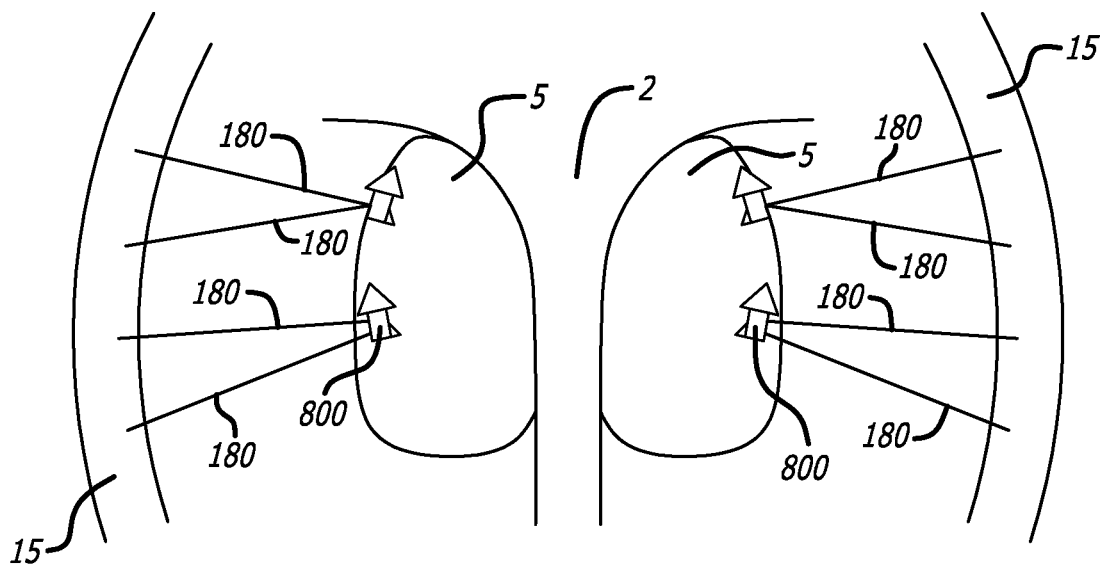
FIG. 18 illustrates yet another embodiment in which suture anchors are used to reduced the narrowing of the urethra according to embodiments of the invention.

FIG. 18 depicts yet another embodiment in which suture anchors 800 are used to reduced the narrowing of the urethra. In this embodiment, multiple suture anchors 800 are delivered to the inside surface of the prostatic capsule 8 and then connected to the pelvic bone 15. Sutures 180 can be tensioned such that the narrowing of the urethra is reduced by displacing the prostatic lobes away from each other. Suture 180 can be connected to pelvic bone by tying the ends of the sutures off one the bone or on connectors (such as k-wires) that are in turn connected to the pelvic bone. According to these embodiments, suture anchors can be placed using minimally invasive surgical techniques of the lower abdomen, in contrast to the trans-urethral approach used in other embodiments disclosed herein.

Certain embodiments disclosed herein include multiple suture anchors delivered to prostatic tissue. Such suture anchors can be delivered in series such that each anchor is connected along one or more segments of suture to the next anchor. Alternately, multiple anchors can each have a discrete segment of suture that is then joined to the next anchor in the series. Sutures as used herein includes conventional surgical suture as well as other connectors of varying rigidity, elasticity, and flexibility.

Advantageously, the volume-occupying characteristics of many of the improved suture anchors described herein are useful in the embodiments designed to be secured in or on prostatic tissue. For example, in the embodiments using multiple anchors in a prostatic lobe in which a second anchors "follows" a first anchor into tissue, the volume-occupying properties of such improved anchors can allow the second anchor to hold securely in tissue.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method of anchoring a suture in tissue, comprising:
providing a suture connected to a suture anchor, the suture anchor comprising a inserting portion, a positioning portion, and a body portion, wherein the body portion has a first configuration and a second configuration;
penetrating tissue in a penetrating direction with the inserting portion; and
tensioning the suture wherein the tensioning induces the positioning portion to orient the suture anchor transverse to the penetrating direction and wherein the tensioning induces the body portion to telescope outwardly to increase the effective volume of the suture anchor.

2. The method of claim 1 wherein the tensioning induces the body portion to pivot to increase the effective volume of the suture anchor.

3. The method of claim 1 where the tensioning induces the body portion to expand in a direction transverse to a longitudinal axis of the suture anchor to increase the cross-sectional area of the suture anchor.

4. A method of anchoring a suture in tissue, comprising:
providing a suture connected to a suture anchor, the suture anchor comprising a inserting portion, a positioning portion, and a body portion, wherein the body portion has a first configuration and a second configuration;
penetrating tissue in a penetrating direction with the inserting portion; and
tensioning the suture wherein the tensioning induces the positioning portion to orient the suture anchor transverse to the penetrating direction and wherein the tensioning induces the body portion to separate from a configuration of nested segments to a configuration of separated segments to increase the effective volume of the suture anchor.

* * * * *